(12) United States Patent
Mason et al.

(10) Patent No.: US 11,589,798 B2
(45) Date of Patent: Feb. 28, 2023

(54) THESEOMETER FOR MEASURING PROPRIOCEPTION PERFORMANCE

(71) Applicant: THE UNIVERSITY OF CHICAGO, Chicago, IL (US)

(72) Inventors: Peggy Mason, Monee, IL (US); Yuri Y. Vieira Sugano, Chicago, IL (US); Austin Hilvert, Bartlett, IL (US); Ashley Riley, Chicago, IL (US)

(73) Assignee: THE UNIVERSITY OF CHICAGO, Chicago, IL (US)

( * ) Notice: Subject to any disclaimer, the term of this patent is extended or adjusted under 35 U.S.C. 154(b) by 349 days.

(21) Appl. No.: 16/707,861

(22) Filed: Dec. 9, 2019

(65) Prior Publication Data
US 2020/0178874 A1 Jun. 11, 2020

Related U.S. Application Data

(60) Provisional application No. 62/777,535, filed on Dec. 10, 2018.

(51) Int. Cl.
*A61B 5/00* (2006.01)
*G06K 9/62* (2022.01)
*H04N 5/225* (2006.01)
*G06T 7/20* (2017.01)
*G06T 7/00* (2017.01)
*A61B 5/11* (2006.01)
*G06V 40/20* (2022.01)

(52) U.S. Cl.
CPC .......... *A61B 5/4082* (2013.01); *A61B 5/0077* (2013.01); *A61B 5/1101* (2013.01); *A61B 5/1114* (2013.01); *A61B 5/1122* (2013.01); *A61B 5/1128* (2013.01); *A61B 5/7264* (2013.01); *G06K 9/6256* (2013.01); *G06T 7/0016* (2013.01); *G06T 7/20* (2013.01); *G06V 40/20* (2022.01); *H04N 5/2253* (2013.01)

(58) Field of Classification Search
CPC .. H04N 5/2257; H04N 5/2253; G06K 9/6256; G06T 7/20; G06T 5/30; G06T 5/002; G06T 7/0016; G06T 7/66; G06T 2207/30196; G06T 2207/20081; G06T 2207/20084; A61B 5/1122; A61B 5/1114; A61B 5/1128; A61B 5/1101; A61B 5/0077; A61B 5/7264; A61B 5/4082; G06V 40/20
See application file for complete search history.

(56) References Cited

U.S. PATENT DOCUMENTS 8,277,396 B2 * 10/2012 Scott .................... A61B 5/1121
600/595
9,149,222 B1 * 10/2015 Zets ...................... A61B 5/4023
9,526,946 B1 * 12/2016 Zets ...................... A61B 5/4023
(Continued)

*Primary Examiner* — Brenda C Bernardi
(74) *Attorney, Agent, or Firm* — Marshall, Gerstein & Borun LLP

(57) ABSTRACT

The disclosure provides a theseometer or proprioceptometer for objectively quantifying the proprioceptive performance of a subject such as a human. The disclosed theseometer is a device comprising a clear, rigid material or screen having or exhibiting a distinguishable target embraced by a series of concentric rings, a digital camera with a lens concentric to the target, a base unit comprising an electronic processor and memory for analyzing data and, optionally, a wheeled base to provide mobility and portability.

20 Claims, 8 Drawing Sheets

(56) References Cited

U.S. PATENT DOCUMENTS

| | | | |
|---|---|---|---|
| 9,763,604 B1* | 9/2017 | Berme | A63B 26/003 |
| 9,867,558 B2* | 1/2018 | Rabischong | A61B 5/4519 |
| 10,117,602 B1* | 11/2018 | Berme | A63B 22/0292 |
| 2008/0108883 A1* | 5/2008 | Scott | A61B 5/1127 |
| | | | 600/300 |
| 2015/0332031 A1* | 11/2015 | Mistry | H04W 12/06 |
| | | | 726/19 |
| 2015/0342517 A1* | 12/2015 | Rabischong | A61B 5/4538 |
| | | | 600/595 |
| 2018/0092534 A1* | 4/2018 | Nabhan | A61B 3/10 |
| 2019/0307217 A1* | 10/2019 | Skahan | A45C 11/00 |

* cited by examiner

THESEOMETER FOR MEASURING PROPRIOCEPTION PERFORMANCE

RELATED APPLICATIONS

This application claims the benefit of U.S. Provisional Application No. 62/777,535, filed Dec. 10, 2018. The entirety of the foregoing provisional application is incorporated by reference herein.

FIELD

The disclosed device relates generally to medical devices. More particularly, the disclosed device relates to devices for measuring proprioceptive performance.

BACKGROUND

At present, proprioceptive measurements of individuals, such as individuals with aberrant neuromuscular behavior, involve directing the individual to point to a target accurately and to hold that point, even in the face of an external load. This test is a typical component of a neurological examination. Currently, the interpretation of an individual's performance on this test is so subjective that virtually any conclusion can be reached. Conventional approaches to the measurement of proprioception in individuals are illustrated in FIG. 1.

The proprioceptive sense is vastly under-studied, arguably because there are no rigorous ways to study proprioception. The conscious appreciation of body position is very poor. Consequently, the typical psychophysical approach used for vision, hearing and the like will not work for proprioception. The sense of proprioception must be assessed using a motor metric.

Currently, motor disorders are typically attributed to problems in motor pathways. It is known, however, that sensory damage can impair motor performance. The case of a certain individual, Ian Waterman, and others with a complete loss of taction and proprioception dramatically, illustrate this point. These individuals (there are about a dozen known in the world), with the exception of Mr. Waterman in his younger years, are all dependent on wheelchairs for mobility, yet they have no damage to their motor pathways or muscles. The lesson here is that proprioception is critical to movement. Patients with unexplained motor deficits may have subtle impairments in proprioception that can be identified with the inventive device disclosed herein. Moreover, incomplete proprioceptive loss that contribute to motor problems are likely to be overlooked at present as there is no way to clearly discover the problem.

Currently available devices are designed to measure 1) the minimal passive movement that a subject can detect; 2) a subject's ability to reproduce a given joint position. Neither of these tasks is of utility in diagnosing motor dysfunction or tracking motor performance in response to treatment. Both are non-ethological, arbitrary tasks that will not tell us about the ability of the person to use proprioception in making movements.

There are devices that test a subject's ability to identify the position of a body part without vision. However, these devices all use an anchor, such as a manipulandum (joystick) that limits the error of the movement. The touch of the manipulandum provides a great deal of information that can make up for any loss of proprioception.

Proprioceptive evaluation is a burgeoning field of research and development. Physicians and researchers currently lack a cheap and effective means of quantifying the extent of a patient's proprioceptive performance.

Accordingly, a need persists in the art for a device that can accurately measure proprioceptive performance in order to identify those individuals that would benefit from appropriate proprioceptive therapies.

SUMMARY

The disclosure provides a device in the form of a theseometer or proprioceptometer that provides objective, accurate measurements of proprioceptive performance in individuals. The device is useful in measuring proprioceptive performance in individuals suffering from such common disorders as diabetic neuropathy, neurological trauma, or a movement disorder, e.g., ataxia or Parkinson's disease. Even individuals with unexplained motor deficits that may have subtle impairments in proprioception can be clearly identified with a theseometer (i.e., proprioceptometer) as disclosed herein. Moreover, the theseometer can detect incomplete proprioceptive loss that contributes to motor problems. In addition, the device can be used with people both with and without vision, such that dysfunction caused by motor or by sensory deficits can be distinguished. The theseometer is inexpensive, simple to manufacture, easy to use, and easily adapted to novel tasks. All of these advantages are attributable to the device's simplicity. This simplicity gives the theseometer or proprioceptometer an inherent advantage over other devices, which are large, delicate, cumbersome, difficult to transport, and not easily grasped by non-experts. The theseometer is a self-contained device capable of measuring proprioceptive performance and analyzing the data without additional equipment. The device is portable due to its light weight, and its mobility can be enhanced by attaching the device to a mobile base such as a wheeled base. Further advantages of the device include the ability to conveniently disassemble the device, an unheard of advantage in the measurement of proprioceptive performance. With the device, proprioceptive function can be measured in patients with relatively common disorders such as diabetic neuropathy, neurological trauma, and movement disorders such as ataxia and Parkinson's disease.

The invention enables testing a subject's ability to use proprioception alone to maintain a position. It also effectively separates out motor from sensory components of motor performance and, thus, of motor impairment. Of note, none of these tests is reproduced by what a neurologist does during an examination. Neurologists ask patients to perform tasks such as holding out their arms and sliding their feet up and down the opposing shin. They look for abnormal movements and resting tremors in order to assess the patient's joint position sense.

The device comprises a base unit that houses an electronic processor and memory sufficient to execute the instructions of a program capable of detecting and plotting position over time, as well as software implementing an algorithm that has been developed to quantify functional, ethologically valid characteristics of sensory motor performance.

The device further comprises a clear support, which can be glass or any type of thermosetting or thermoplastic clear plastic such as polycarbonate, acrylic, Plexiglas, Lucite, and the like. Also contemplated are translucent and opaque supports as well as discontinuously solid supports such as meshes or screens. In a typical configuration, the support appears as a pane of any suitable size and shape, but preferably rectangular, which may be attached to a stand, such as a mobile stand (e.g., a rolling stand). The pane comprises a target point or area, which is typically centered in the pane. The target may be a round dot and the target may be colored, e.g., red, to increase its visibility. Disposed about the target are concentric circles of defined, or measurable, radii. In use, the target and concentric circles provide landmarks for distance calculations used in objectively measuring the proprioceptive abilities of a subject. An exemplary embodiment of the device is shown in FIG. 2 herein.

In one aspect, the disclosure provides a theseometer device comprising (a) a distinguishable target mark and a series of concentric rings disposed about the target mark, each of the distinguishable target mark and series of concentric rings exhibited via a planar surface; (b) a digital camera comprising a lens concentric to the distinguishable target mark; and (c) a base unit comprising an electronic processor and memory. In some embodiments, the planar surface is a screen of a mobile device.

In an additional aspect, the disclosure provides a theseometer device comprising: (a) a clear planar material comprising a distinguishable target mark and at least three concentric rings disposed about the target mark; (b) a digital camera comprising a lens concentric to the distinguishable target mark; and (c) a base unit comprising an electronic processor and memory. In some embodiments, the clear planar material is plastic, such as poly (methyl methacrylate), butyrate, polycarbonate, polystyrene, or polyester. In some embodiments, the clear planar material is rigid or is a flexible film, which may be attached to a frame that prevents movements of the film that may distort measurements. In some embodiments, the digital camera is attached to a support arm, such as a support arm that is articulable. In some embodiments, the base unit further comprises software for tracking the movement of a pointing body part. In some embodiments, the base unit further comprises software for detecting a tremor in a pointing body part. In some embodiments, the theseometer as disclosed herein is capable of measuring the distance between the end point of a pointing body part and the target mark to a precision within 1.0 millimeter.

Another aspect of the disclosure is drawn to a method of assessing the proprioceptive performance of an individual comprising: (a) having the individual use a pointing body part to point to a distinguishable target mark on the clear material of a theseometer device as described herein; (b) recording the position of the pointing body part; (c) analyzing the position of the pointing body part relative to the distinguishable target mark; and (d) assessing the proprioceptive performance of the individual based on the analysis. In some embodiments, the pointing body part is a fingertip, a finger, a hand, an arm, a shoulder, a toe, a foot, a leg, a head or a chin. In some embodiments, the position of the pointing body part is detected over time, resulting in the determination of a trajectory of the pointing body part. In some embodiments, the pointing body part is associated with an accessory pointing device, such as having the accessory pointing device attached to the pointing body part or having the accessory pointing device worn by the pointing body part. An exemplary accessory pointing device is a lightweight, plastic or fabric finger cap of contrasting color. In some embodiments, the detection of the pointing body part over time results in the detection of a tremor. In some embodiments, the individual has diabetic neuropathy, Parkinson's disease, neurological trauma, or a movement disorder, such as ataxia or Parkinson's disease. In some embodiments, the diabetic neuropathy, neurological trauma, or movement disorder was undiagnosed prior to assessing proprioceptive performance. In some embodiments, the method of assessing the proprioceptive performance of an individual may further comprise training a machine learning model with a plurality of images depicting sets of distinguishable target marks and corresponding body parts of individuals, wherein the processor implements the machine learning model to assess, by the processor, the proprioceptive performance of the individual based on the analysis.

A still further aspect of the disclosure is drawn to a method of assessing a proprioceptive performance of an individual comprising: (a) recording, into a memory of a theseometer device, a position of a pointing body part of the individual, where the theseometer device comprises a distinguishable target mark and a series of concentric rings disposed about the target mark, each of the distinguishable target mark and series of concentric rings exhibited via a planar surface, and wherein the individual points with the pointing body part to the distinguishable target mark; (b) analyzing, by a processor, the position of the pointing body part relative to the distinguishable target mark; and (c) assessing, by the processor, the proprioceptive performance of the individual based on the analysis of the pointing body part relative to the distinguishable target mark.

Generally, with respect to various embodiments herein, a theseometer device may be used or configured to determine proprioceptive performance of individuals as follows. A participant or other individuals will be positioned (e.g., standing or sitting) in front of the theseometer device during two sessions. One session is conducted with the participant's eyes open. A second type of session is conducted with the participant's eyes closed. Each session may be set for a pre-determined duration (e.g., 60 seconds). Both types of sessions may be performed on each limb. Before starting a session, the participant may be instructed to point, with a body part (e.g., a finger) to a center of a set of concentric circles, e.g., a distinguishable target mark, which may be positioned or exhibited on a clear slab of Plexiglas. On the other side of the glass, a digital camera or webcam may capture lateral, vertical, diagonal, or other such movement of the body part (e.g., a finger) as it moves over time during the session(s). The data is captured, recorded, or otherwise saved as digital trail. The trail may be saved, e.g., in a memory, for later analysis to determine proprioceptive performance of the participant, or other such determinations as described herein.

The theseometer device, and its related methods and uses, may be used or implemented in various tests, with respect to various body parts or portions of individuals, during medical or diagnostic procedures or trials. For example, theseometer device, and its related methods, may be implemented to determine how, and to what degree of, proprioceptive function in a shoulder correlates with the presence or absence of foot neuropathy of an individual. For example, through trials and sessions as described herein, a theseometer device, and its related methods and uses, may be used or implemented to determine whether proprioceptive function of an individual's shoulder joint is diminished in patients with known diabetic neuropathy of the foot. As a control group, such determinations may be may also be compared with recently diagnosed diabetic patients with no clinical sign of foot problems. In similar trials, testing or sessions with the theseometer device, may include determining or assessing proprioceptive function in the ankle joint as compared to other portions of the body (e.g., a shoulder).

In additional embodiments, the theseometer device, and its related methods and uses, may be used or implemented in various tests, and with respect to various body parts or portions of individuals, for predicting development of distal nerve dysfunction within individuals. For example, a theseometer device, as disclosed herein, may be configured or implemented to determine whether proprioceptive function diminishes in patients in anticipation of the development of diabetic neuropathy in a given body part, e.g., at foot or shoulder. For example, a determination, by implementation of a theseometer device, may identify a decrease in shoulder proprioception performance. Such determination may be used, e.g., by the theseometer device, to predict the development of more distal nerve dysfunction. In some embodiments, such test or assessment may establish a baseline for a given patient, where a patient without any sign, or with low signs, of diabetic neuropathy may then be followed in a prospective study. In such embodiments, assessments at regularly scheduled visits to a clinic may be compared to disease progression to determine whether proprioceptive function is diminishing in patients in anticipation of a development of diabetic neuropathy in a given body part.

Generally, a theseometer device, and its related methods and uses, provide numerous medical and treatment related benefits. For example, as described herein, the theseometer device, and its related methods and uses, may be used to detect, diagnose, predict, or otherwise determine diabetes. Diabetes mellitus is an escalating global problem as the number of patients is growing rapidly in developing countries and continues to climb in developed countries. The most common complication of diabetes is neuropathy, leading to foot ulcers that are costly to treat, recur in more than 50% of cases, and ultimately require amputation in a large number of patients. Nearly twenty years ago, diabetic foot care cost the United States $10.9 billion (in today's dollars) to treat. Currently, the cost of a patient with diabetic neuropathy is approximately four times greater than the cost of a diabetic patient without such a complication. In addition, the medical costs of treatment are generally far less than the costs associated with patients dropping out of the work force, becoming disabled, and/or altering family productivity due to a loss of quality of life.

Conventional techniques fail to correctly determine, diagnose, or predict diabetes. For example, glycemic control, as related to diabetes, generally correlates with the incidence of diabetic neuropathy but is not predictive. Thus, while patients with poor control have a higher risk than those with moderate to good control, even patients in the latter group eventually may develop neuropathy. Physicians are currently unable to pinpoint which of their patients will develop a neuropathy. Instead, a first sign of neuropathy trouble is typically a well-developed foot ulcer. In such cases, physicians are then disadvantaged because they must then treat a well advanced disease process.

The theseometer device, and its related methods and uses, as described herein are able to detect, diagnose, predict, or otherwise determine diabetes in advance. As described herein, a theseometer device may be implemented to assess performance on an upper or lower limb pointing task when the eyes of a patient are either open or closed. The difference in performance between these two conditions (i.e., eyes opened or closed) is attributable to the ability of proprioceptive feedback, of a patient, to guide bodily movement. The test conducted with the theseometer device substitutes for the current standard, which is a painful and expensive procedure known as a nerve conduction study or EMG testing. Instead, the test conducted with the theseometer device as described herein tracks large-fiber nerve function across patient visits, which allows physicians to determine foot or other bodily problems early in diabetic patients, before such problems arise, such as severe problems that require amputation or other severe treatments.

Other features and advantages of the invention will be apparent from the following detailed description and figures, and from the claims.

BRIEF DESCRIPTION OF THE DRAWINGS

The Figures described below depict various aspects of the system and methods disclosed therein. It should be understood that each Figure depicts an embodiment of a particular aspect of the disclosed system and methods, and that each of the Figures is intended to accord with a possible embodiment thereof. Further, wherever possible, the following description refers to the reference numerals included in the following Figures, in which features depicted in multiple Figures are designated with consistent reference numerals.

There are shown in the drawings arrangements which are presently discussed, it being understood, however, that the present embodiments are not limited to the precise arrangements and instrumentalities shown, wherein:

FIG. 1 illustrates each of ankle (A), knee (B), and shoulder (C) techniques, all individually being assessed using TTDPM. In addition, FIG. 1 further illustrates each of ankle (D), knee (E), and shoulder (F) techniques, all individually being assessed using JPR. Further, FIG. 1 illustrates each of ankle (G), knee (H), and shoulder (I) techniques, all individually being assessed using AMEDA.

As illustrated in FIG. 2, in some embodiments, base unit 210 may be attached to, or otherwise configured with, one or more of any of theseometer device 202, support arm 209, and/or vehicle support 220.

The Figures depict preferred embodiments for purposes of illustration only. Alternative embodiments of the systems and methods illustrated herein may be employed without departing from the principles of the invention described herein.

DETAILED DESCRIPTION

Figure 1:
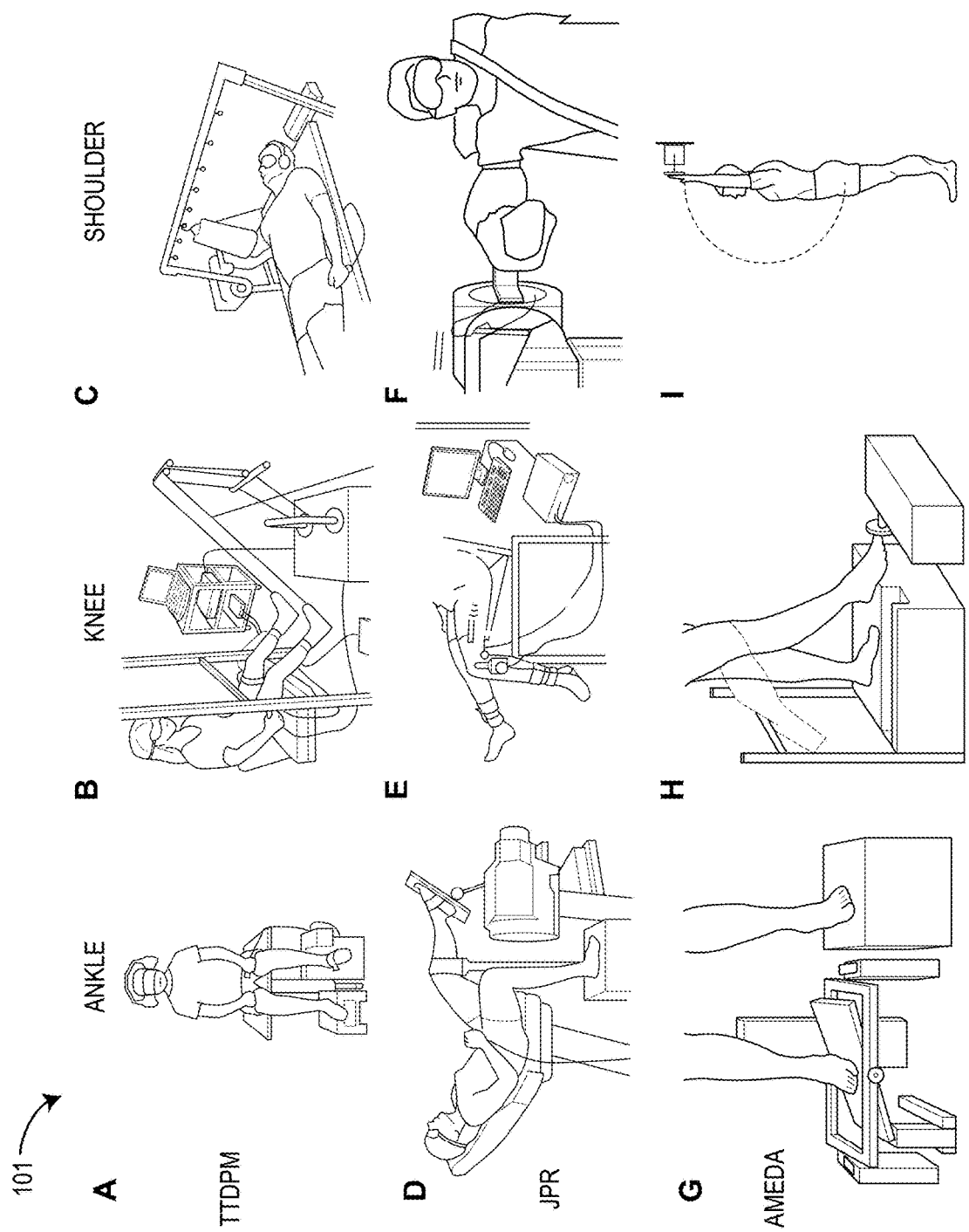
FIG. 1 is a schematic illustration of conventional testing techniques 101 for assessing proprioception of various body parts. The illustrated conventional testing techniques 101 include the Threshold to Detection of Passive Motion (TTDPM), Joint Position Recognition (JPR), and the Active Movement Extent Discrimination Assessment (AMEDA). The body parts illustrated include the ankle, knee and shoulder. As shown.
Figure 2:
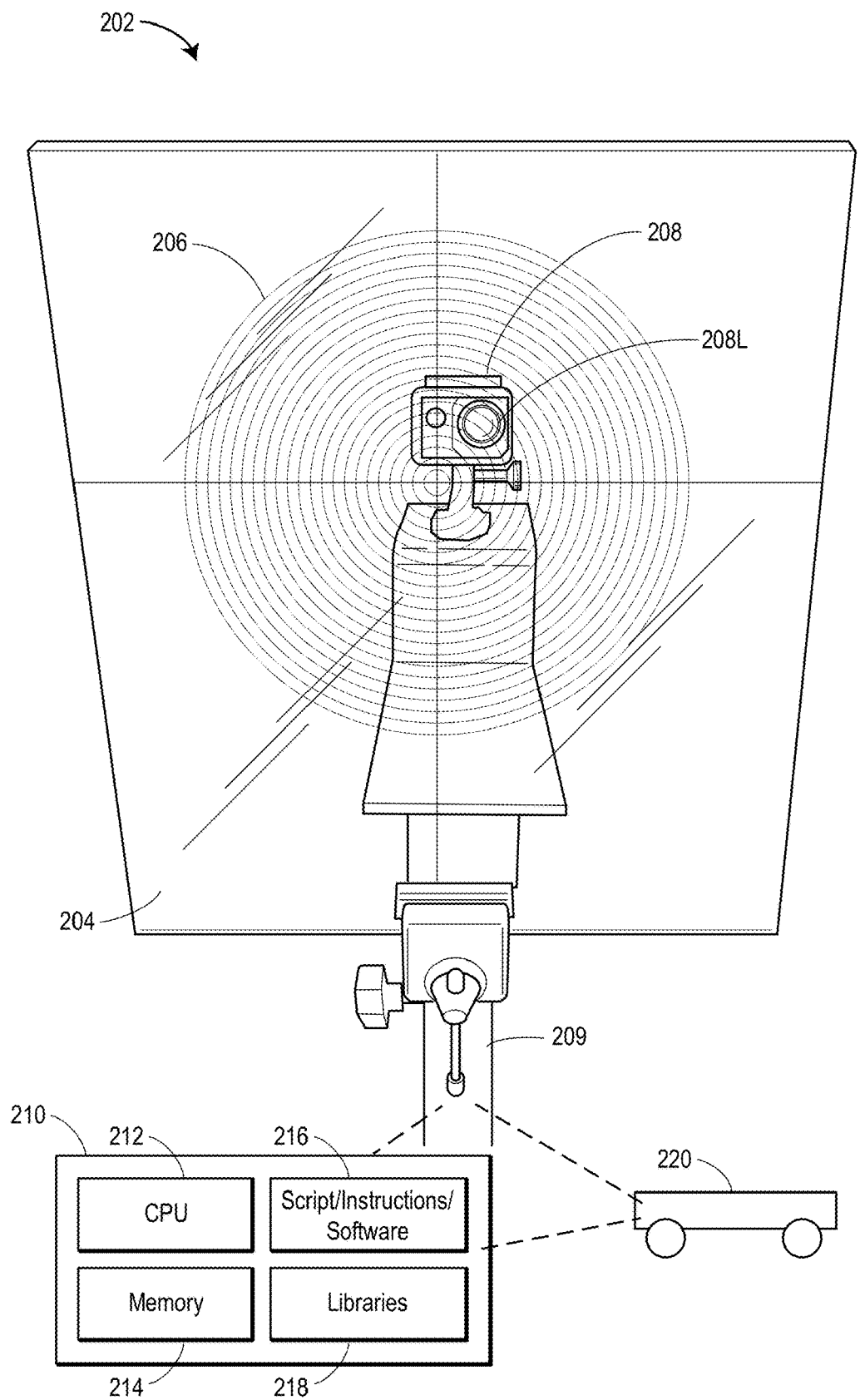
FIG. 2 illustrates an embodiment of a theseometer device 202 (i.e., a proprioceptometer device). In the embodiment of FIG. 2, the theseometer device 202 includes a planar surface 204, which, as depicted in the embodiment of FIG. 2, is an example clear material (rigid Plexiglas) exhibiting a target, which is shown as distinguishable target mark 206, having a distinguishable target shape in the form of a red dot centered within a series of concentric circles of known, or measurable, radii, diameters and/or inter-ring separations. Concentrically aligned with the target is the lens 208L of a digital camera 208 capable of recording an image or images of the clear material and/or a body part, such as a finger, which may be located on the opposite side of the clear material from the camera. In some embodiments, the digital camera is attached to a support arm 209 that may be rigid or articulable and may be made of any suitably stable and rigid material such as plastic, wood or metal. The theseometer device may further include a wheeled vehicle support 220 for positioning the theseometer device and providing mobility and portability. In various embodiments, theseometer device 202 may comprise a base unit 210. Base unit 210 may include an electronic processor 212 (i.e., central processing unit (CPU)) and a memory 214. Base unit 210 may further include scripts, instructions, and/or software 216, as described herein, that may be stored in memory 214 and/or executed by processor 212. Base unit 210 may further include software libraries 218, as described herein, that may be stored in memory 214 and/or executed by processor 212. Software libraries 218 may be used with, such as compiled with or interpreted with, the scripts, instructions, and/or software 216 for implementation of the algorithms, methods, flowcharts, as described herein, such as for assessing a proprioceptive performance of an individual. In still further embodiments, base unit 210 may be communicatively coupled, in a wireless or wired manner, with digital camera 208. For example, digital camera 208 may send signals images, videos, or otherwise data to base unit 210 for storage in memory 214 and/or for processing by processor 212 as described herein.

The disclosed invention, as provided in various embodiments herein, is a device that can quantify proprioceptive performance in humans. Generally, the device (e.g., theseometer device 202) uses a distinguishable target shape (e.g., distinguishable target mark 206) that may be exhibited on or via a planar surface, such as display screen of a mobile device, planar material, etc. For example, in some embodiments, the device is composed of a clear material such as plastic, e.g., Plexiglas, that contains a target in the form of a distinguishable target shape (e.g., distinguishable target mark 206), such as a colored, e.g., red, dot. The clear material may be a flexible film or a rigid, approximately planar, sheet-like material. In various embodiments, the target is central to a series of concentric circles, but need not be centered on the clear material. Preferably, the clear material is rectangular in shape and the device can be advantageously located on a wheeled vehicle such as a rolling stand or cart to provide portability (e.g., vehicle support 220). In such embodiments, the clear material, e.g., rigid Plexiglas, is attached, directly or indirectly, to the wheeled vehicle, for example, as illustrated by FIG. 2. In some embodiments, the device further comprises a digital camera (e.g., digital camera 208) having a lens (e.g., lens 208L) that is concentric to the target. In some embodiments, the camera is rigidly or movably mounted to the wheeled vehicle such that the camera lens is concentric with the target. Images captured by the camera are recorded directly to a processing board contained within the device (e.g., within digital camera 208 and/or base unit 210), or may be recorded on any compatible memory media (e.g., memory 214), such as a memory card, preferably of high-capacity.

In various embodiments, the device is implemented as a theseometer or proprioceptometer (e.g., theseometer device 202) that quantifies proprioceptive performance in subjects such as humans. In certain aspects, theseometer device may be used to assess neuronal health. In particular, assessments of neuronal health using the theseometer device provides a testing or treatment procedure, referred to herein as "The NerveMetric," which serves as a test by which a participant may be measured to determine large fiber nerve health. Each session of the may test last for a brief period of time, such as 60 seconds.

For example, in some embodiments, a participant or individual may be positioned (e.g., standing or sitting) in front of a theseometer device (e.g., theseometer device 202) in two sessions. For example, as described herein for FIGS. 3 and 4, in a first session, the participant will have his or her eyes open. In the second session, the participant will have his or her eyes closed. Before starting the 60 second session, the participant may be instructed to point to a center of a set of concentric circles (e.g., distinguishable target mark 206) on a planar surface (e.g., planar surface 204), such as clear slab of Plexiglas. On the other side of the glass, a digital camera (e.g., digital camera 208) may capture the lateral, vertical and diagonal movement of a body part, e.g., a finger, as it moves. The images and/or data from the test may be saved, e.g., in memory 214, for later analysis as described herein, for example, as described and illustrated for any of FIGS. 3 through 8.

In various embodiments, a theseometer device (e.g., theseometer device 202), as disclosed herein, generally includes various pieces of hardware with software installed on the hardware and a customized mount and stand (e.g., vehicle support 220). For example, in various embodiments, the theseometer device includes a base unit (e.g., base unit 210) comprising an electronic processor (e.g., processor 212) and a memory (e.g., memory 214). Further, in various embodiments, recording apparatus, e.g., a digital camera 208, is part of the theseometer device and is typically configured in a mounting (e.g., support arm 209) attached to the base unit (e.g., base unit 210).

In some embodiments, theseometer devices, as disclosed herein (e.g., theseometer device 202), may comprise hardware components supplied by, and/or operable with hardware of, RASPBERRY PI. For example, at least in one embodiment, a theseometer may comprise components or pieces including, e.g., a RASPBERRY PI Model 3 B+ device (e.g., as base unit 210), a RASPBERRY PI seven-inch touchscreen display, a RASPBERRY PI Camera Module VV2 (e.g., as a digital camera 208), and a 128 GB SAMSUNG secure digital (SD) card (or other such SD, flash card, or memory) (e.g., as memory 214) communicatively coupled to a microprocessor (e.g., processor 212) of the RASPBERRY PI unit or device. This configuration may correspond to base unit 210 and its related components as described herein for FIG. 2. In some embodiments, this hardware, which may be configured with other hardware or structural components as described herein, may be placed for support on a customized, movable mount (e.g., vehicle support 220). With respect to this configuration, the microprocessor may be mounted to the touchscreen's back by screws and the camera module may be connected to the RASPBERRY PI device by an approximately 8-inch ribbon cable. It is to be understood, however, that other similar hardware components and/or ribbon cables may be used to configure a theseometer device 202 in accordance with the disclosed embodiments herein.

In various embodiments, a mount (e.g., support arm 209) supports the hardware and may also provide a layer of protection for the hardware, for example, in the form of a planar surface, e.g., a piece of Plexiglas, as described herein. An ancillary benefit of this planar surface, e.g., Plexiglas, is that it serves as a visual guide. That is, as described herein, the Plexiglas (or other such planar surface) may contain layers of concentric circles around its center (e.g., distinguishable target mark 206), and the participant is typically instructed to point to the middle of that target of concentric circles. The stand itself may be moveable (e.g., via vehicle support 220), allowing the whole piece to travel where needed.

The inclusion of a recording apparatus (e.g., a digital camera 208) in the device (e.g., digital camera 208) provides at least four advantages over known approaches to assessing proprioception. First, the recording device can record positional information over time, revealing movement trajectories (e.g., as illustrated by FIGS. 5 through 8, herein) that are not captured by approaches focused exclusively on end-point information. Second, the camera (e.g., digital camera 208) is capable of capturing small movements and/or fleetingly quick or brief movements, such as capturing tremors in a pointing body part. Third, the use of a recording apparatus (e.g., digital camera 208, base unit 210, and/or memory 214) provides an objective measure of body position or pointing, eliminating the subjectivity involved in conventional techniques where a human marks where a subject is pointing. Fourth, the recording apparatus (e.g., digital camera 208, base unit 210, and/or memory 214) provides improved accuracy in identifying a location to which a subject is pointing relative to using concentric bands (e.g., distinguishable target mark 206) that are, e.g., 4 centimeters wide and the hand-marking of pointing spots using adhesive dots large enough to be conveniently manipulated by the human hand (e.g., 0.5-inch diameter). Once data is recorded using the recording device (e.g., digital camera 208, base unit 210, and/or memory 214), processor 212 executing software (e.g., software 216 and/or software libraries 218) implementing an algorithm (as illustrated in the flowchart shown in FIG. 3), may assesses proprioceptive performance of the individual. In addition, processor 212 may execute software implements an algorithm for assessing tremor, as illustrated in the flowchart shown in FIG. 4.

As but one example of the improvement of the disclosed device relative to conventional approaches to proprioception, the disclosed device is compared to the STARmat approach to assessing proprioception. STARmat has no recording device, which means that the STARmat methodology is constrained to a single output, e.g., the average position of three trials, as it is currently configured. Thus the quantification of motor and proprioceptive performance provided by the disclosed device is not available when using the STARmat approach. The STARmat system only measures end point data, as noted above. It does not record trajectory, and thus much proprioceptive information is lost. Also, with the STARmat device, tremor is not detectable. Moreover, there is a large amount of subjectivity in where the investigator marks the trial. This weakness affects both the end position task and the trace-a-clock task. Additionally, precision is limited in the STARmat system because zones of 4 cm in width are used in recording results, whereas the disclosed device is precise to less than a millimeter, with detection zones of 5 mm and a resolution that is an order of magnitude better, or about 0.5 mm and is routinely less than 1.0 mm.

There are at least two more procedural differences between the STARmat system and the disclosed device. First, the STARmat task conflates postural sway with limb proprioception, in contrast to the disclosed device. Subjects stand in the STARmat approach, but typically sit when being examined with the disclosed device. Second, STARmat does not test subjects with their eyes closed as well as open (related to the standing position). Thus the STARmat system cannot distinguish sensory and motor problems.

The embodiments of the present disclosure overcome the limitations of the STARmat system. For example, with respect to theseometer device (e.g., theseometer device 202) of the present disclosure, various tests (e.g., as illustrated and described for FIGS. 3 through 8) are performed by asking subjects to point to the target (e.g., distinguishable target mark 206) using a bodily appendage under different experimental conditions, such as having their eyes open or closed or placing a small weighted load on the pointing appendage. The device (e.g., theseometer device 202) is amenable to pointing using any body part or appendage, including a finger(s), hand, arm, shoulder, head, toe, foot or leg. In some embodiments, the subject wears, on their pointing body part, an accessory pointing device that can be detected by the recording device. Such an accessory pointing device can improve the detection of depth, and can help to ensure that background will not interfere with tracking. This accessory pointing device can made of inexpensive lightweight material, such as plastic or fabric, and in a color that has high contrast with the background, including but not limited to, black and/or bright red. In some embodiments, the algorithm assessing proprioception is informed of the color of the accessory pointing device. The accessory pointing device is intended to be lightweight to reduce load.

Figure 3:
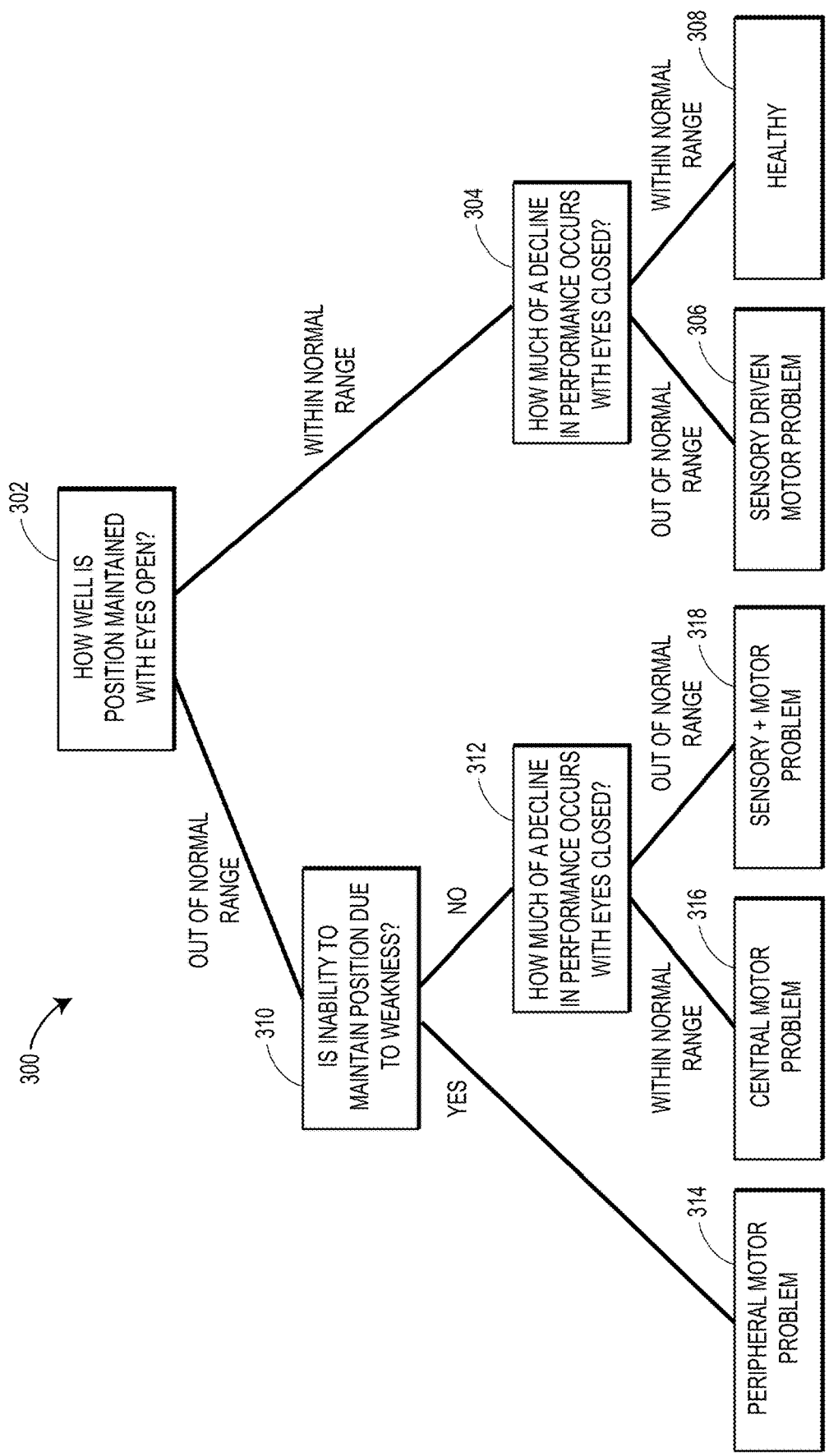
FIG. 3 is an example flowchart illustrating the software logic 300 that may be incorporated into a theseometer device (e.g., theseometer device 202) to assess proprioception as described in various embodiments herein. The software logic 300, as implemented via theseometer device 202, assesses the ability of an individual to maintain a position with eyes open (302), determines whether any inability to maintain position with eyes open is due to physical weakness (310), and assesses the degree of decline in performance resulting from performance with eyes closed (304 or 312) to determine whether there is a peripheral motor problem (314), a central motor problem (316), a sensory-and-motor problem (318), a sensory-driven motor problem (306), or the individual is healthy (308). It is recognized that the maintenance of position with eyes open is not suitable for visually impaired or paralyzed individuals. Also, in assessing whether failure to maintain position is due to weakness, a metric from the data obtained (e.g., the standard deviation of angular components in instantaneous vectors) can be used to evaluate weakness. Alternatively, one of several conventional methods for determining weakness could be used. The software logic 300 may be executed in either an "out of normal range" state or a "within normal range" state.
Figure 4:
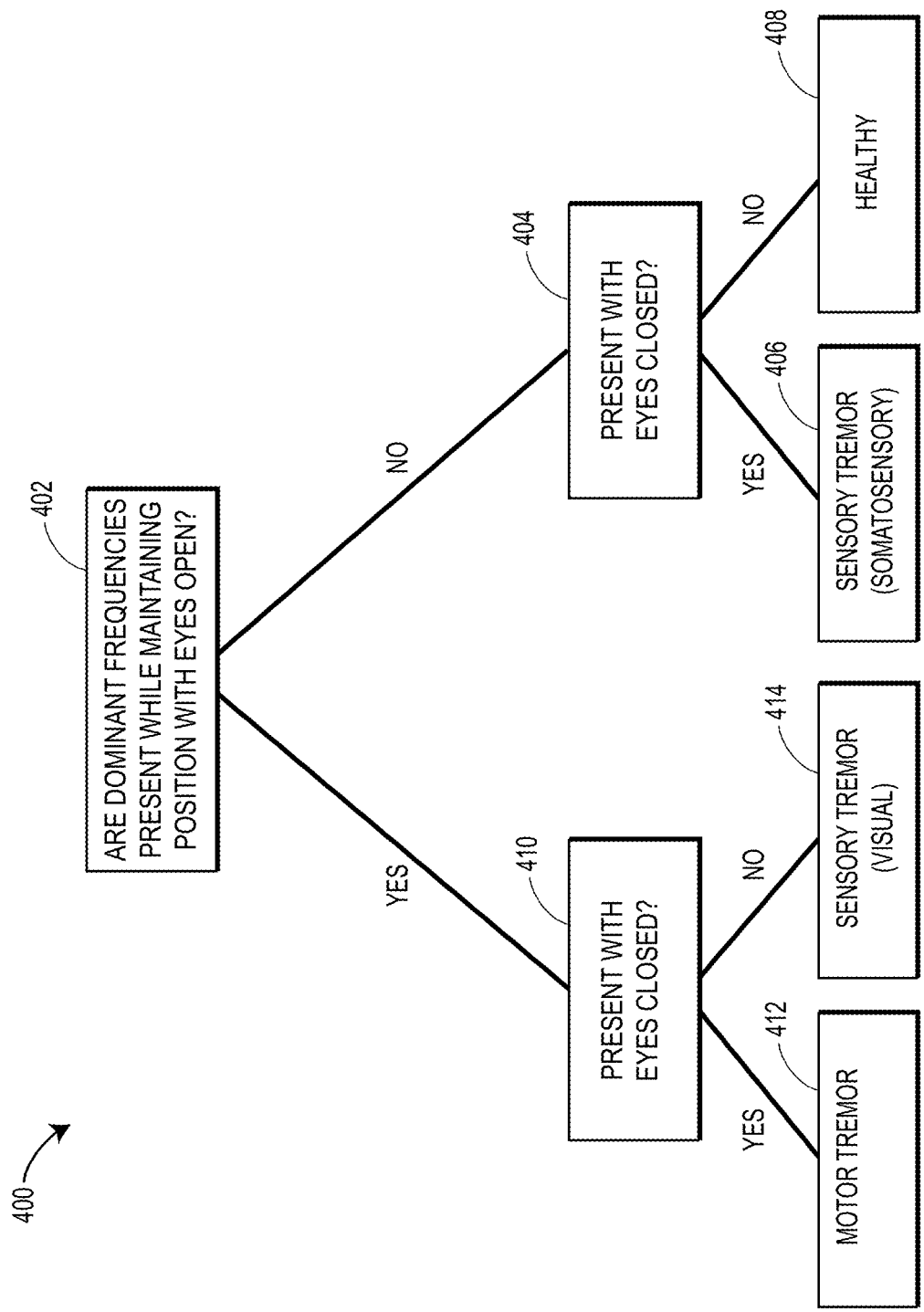
FIG. 4 is an example flowchart showing the software logic 400 for assessing, with theseometer device 202, tremor(s) involving an assessment of dominant tremor frequencies observed with eyes open (402) and an investigation of whether the tremor frequencies persist with eyes closed (404 and 410) to determine whether there is a motor tremor (412), a sensory (visual) tremor (414), a sensory (somatosensory) tremor (406), or the individual is healthy (408).
Figure 5:
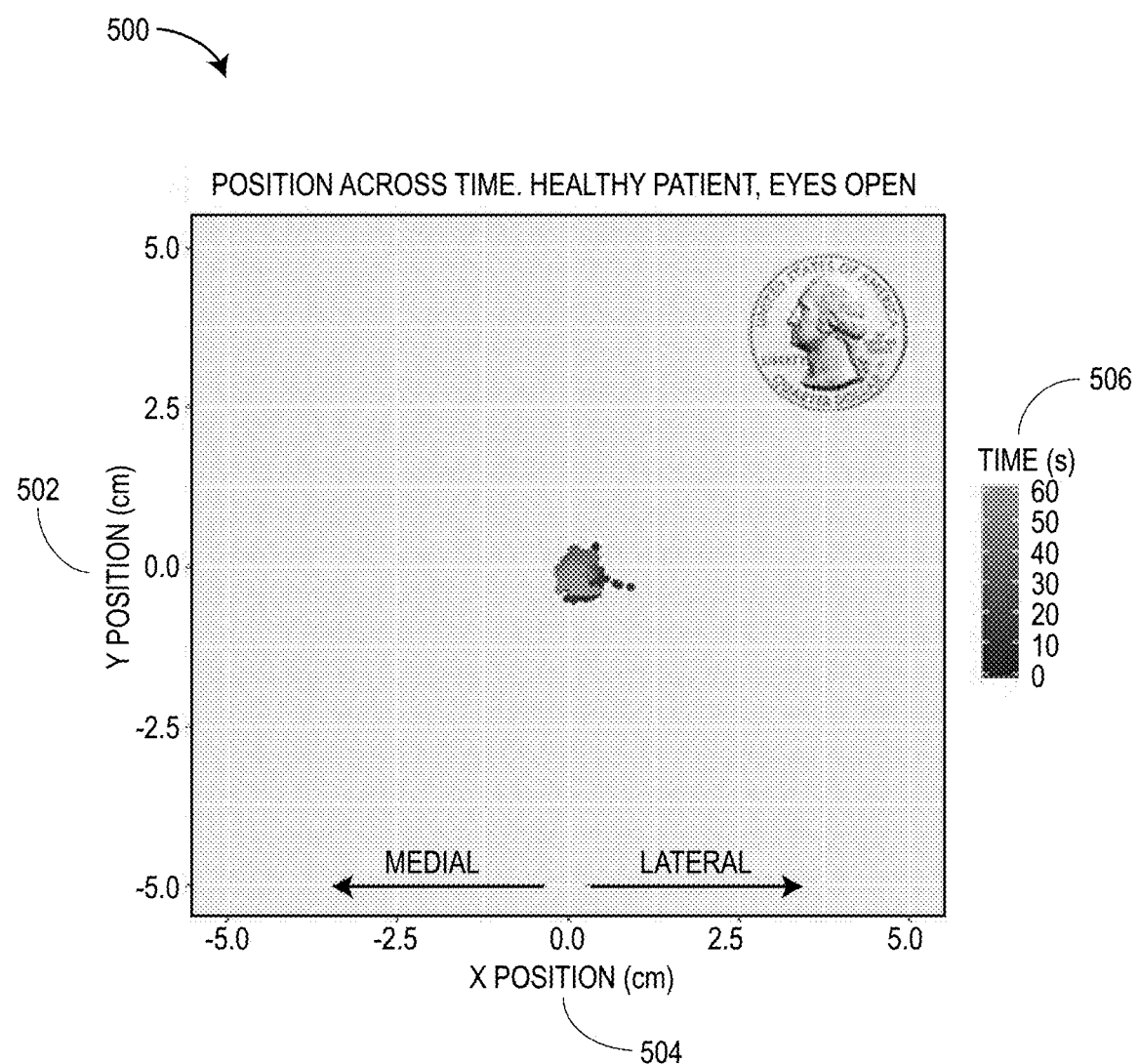
FIG. 5 is an example two-dimensional plot 500 of pointing position (including a y-position 502 and an x-position 504 in centimeters) of an individual across time of a healthy patient with eyes open. Time in seconds is indicated by the shaded gray scale 506 at right. For comparison, the real-size image of a U.S. quarter is provided in the upper right of the grid for relative area comparison.
Figure 6:
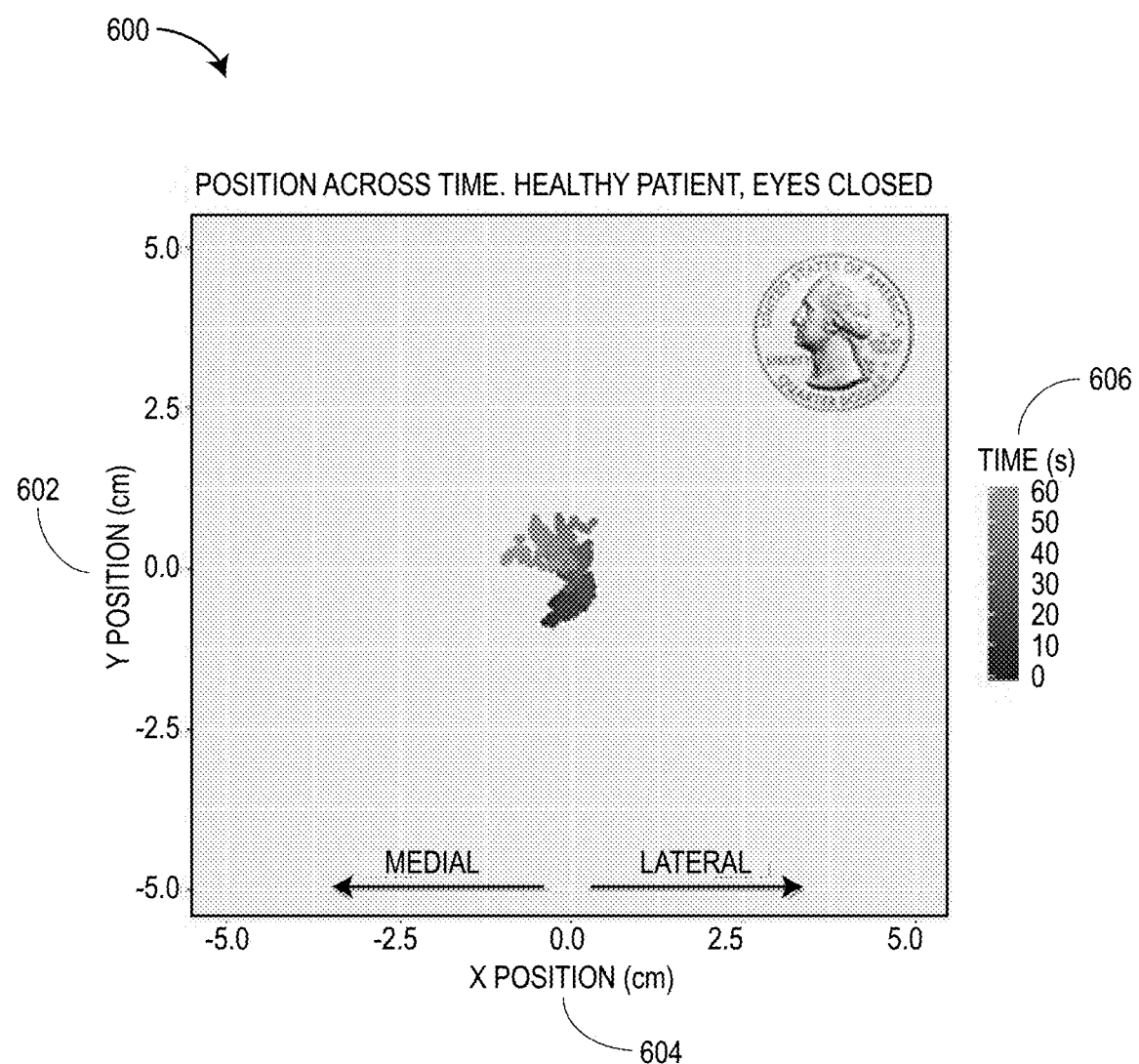
FIG. 6 is an example two-dimensional plot 600 of pointing position (including a y-position 602 and an x-position 604 in centimeters) of an individual across time of a healthy patient with eyes closed. Time in seconds is indicated by the shaded gray scale 606 at right. For comparison, the real-size image of a U.S. quarter is provided in the upper right of the grid for relative area comparison.
Figure 7:
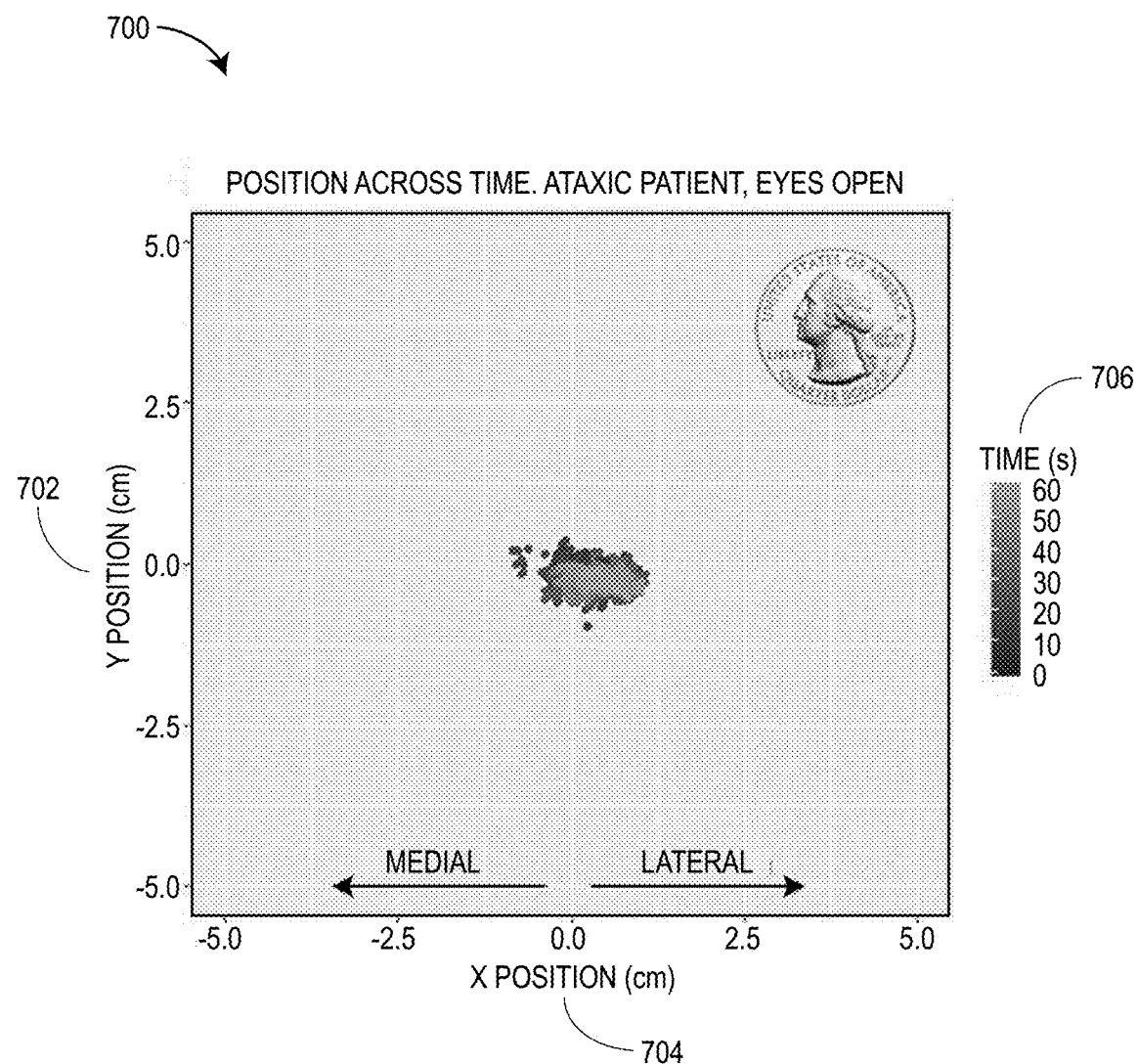
FIG. 7 is an example two-dimensional plot 700 of pointing position (including a y-position 702 and an x-position 704 in centimeters) of an individual across time of an ataxic patient with eyes open. Time in seconds is indicated by the shaded gray scale 706 at right. For comparison, the real-size image of a U.S. quarter is provided in the upper right of the grid for relative area comparison.
Figure 8:
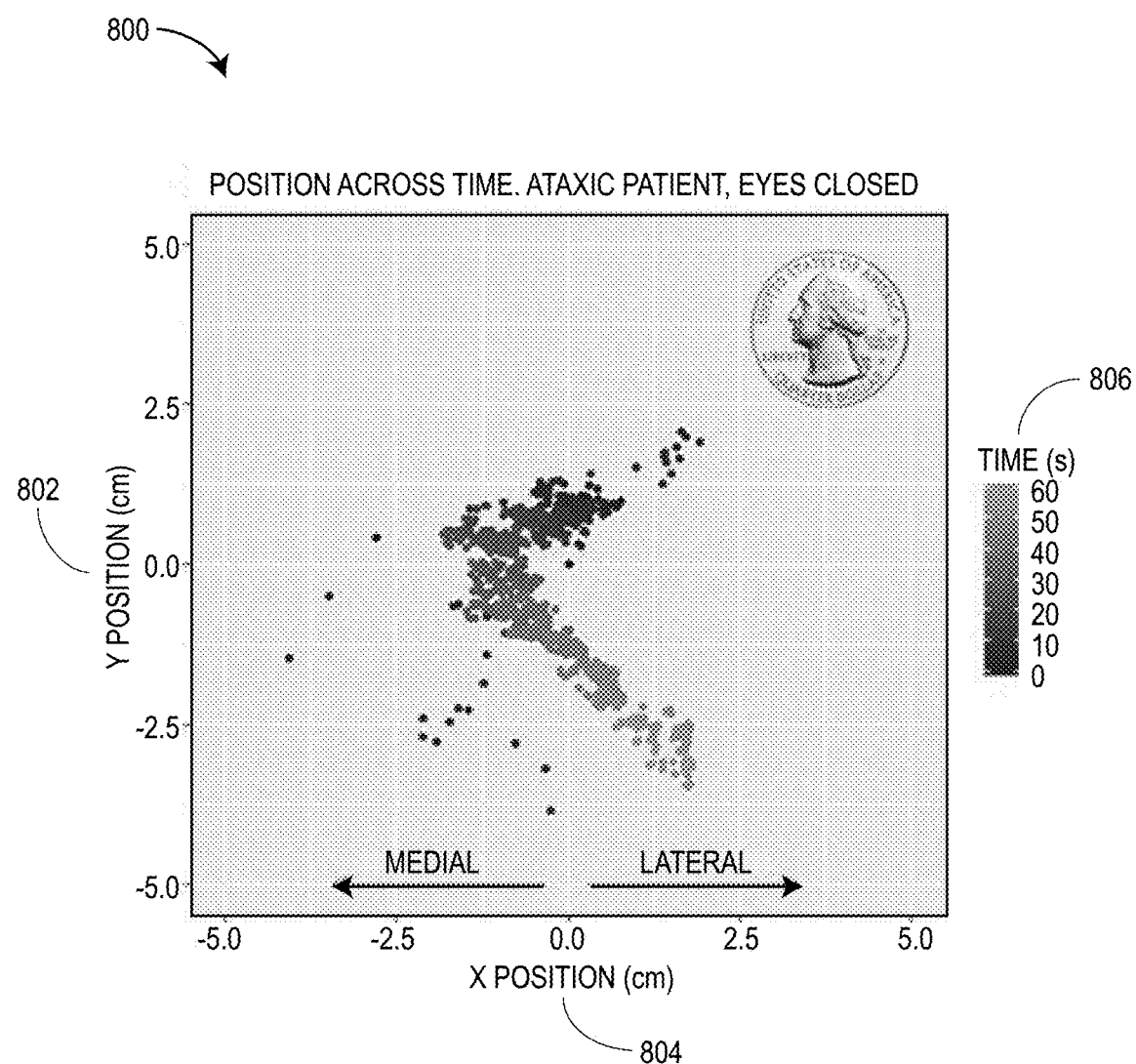
FIG. 8 is an example two-dimensional plot 800 of pointing position (including a y-position 802 and an x-position 804 in centimeters) of an individual across time of an ataxic patient with eyes closed. Time in seconds is indicated by the shaded gray scale 806 at right. For comparison, the real-size image of a U.S. quarter is provided in the upper right of the grid for relative area comparison.

In some embodiments, the subject is asked to point to the target (e.g., distinguishable target mark 206) for a period of time (e.g., 60 seconds), with either eyes open or closed. The time is arbitrary, and further data collection methods may utilize varying times of assessment. The upper limit of time assessment will be related to muscle fatigue. Fingertip location may be tracked with computer software (e.g., software 216 and/or software libraries 218) and the trajectory analyzed and compared between subjects. For example, in one embodiment, software provided by EthoVision is available to track and analyze motion in two dimensions. In other embodiments, open source computer vision (open CV) algorithms or software (e.g., software 216 and/or software libraries 218) may be used to live-track the finger in three dimensions without the use of third-party software. Various output metrics, which may be recorded or stored in memory 214, include but are not limited to total excursion, duration within radially concentric zones of 5 millimeters, time in central zone, latency to leave central zone, most peripheral zone reached, distance to origin, final position vector, X and Y (and in 3d embodiments, Z) coordinate variance, dominant tremor frequency, and time spent in each quadrant. In general terms, a device (e.g., theseometer device 202) may execute software (e.g., software 216 and/or software libraries 218) to implement an algorithm assessing proprioception, as shown by the flowchart in FIG. 3, and may execute software (e.g., software 216 and/or software libraries 218) to implement an algorithm to assess tremor, as illustrated in FIG. 4. The device (e.g., theseometer device 202) can also measure an individual's sensitivity to load. This is accomplished through a sinusoidal application of force while the subject is asked to keep their position steady.

The device (e.g., theseometer device 202) may be used in performing various tests that require subjects to point with a body appendage, e.g., a finger, arm, shoulder, head, toe, foot, knee or leg, with or without an attached or grasped pointing device, to the target under different experimental conditions, such as when their eyes are open or closed (e.g., as described for FIGS. 3 and/or 4 herein), or when a relatively small weighted load is placed on the pointing appendage or pointing device. An additional experimental condition is the length of time a subject is required to point, for example by having the subject point to the target for 5 seconds, 10 seconds, 15 seconds, 30 seconds, one minute or longer, with either eyes open or closed and the small weighted load in use or not. The pointing time may vary according to the data collection method, the appendage used to point, and the condition of the subject. The upper limit of time assessment is set by muscle fatigue. The body part used to point to the target (e.g., distinguishable target mark 206), such as a fingertip, has its location tracked with computer software (e.g., software 216 and/or software libraries 218) analyzing the data recorded by the camera (e.g., digital camera 208) to construct the trajectory of the pointing body part, which is in contrast to existing schemes for assessing proprioception that rely exclusively on end-point data. The trajectory is analyzed and may be compared between subjects, for example, as described for FIGS. 5 through 8 herein.

In an exemplary embodiment, EthoVision software may be used to track and analyze motion in two dimensions. In additional embodiments, as described herein, the use of open source computer vision (open CV) algorithms are implemented to live-track the pointing body appendage (e.g., a finger) in three dimensions without the use of third-party software. Software scripts (e.g., software 216) for performing the algorithms or methods described herein may be implemented in various programming languages, including Python, R, C++, Java, and the like. In addition, the scripts may use various software libraries (e.g., software libraries 218), such as compile or interpret libraries, for tracking and analyzing images and motion for the purposes described herein. For example, in one embodiment, where the programming language used is Python, a related set of software libraries (e.g., software libraries 218) used for tracking and analyzing images and motions includes (but is not limited by nor bound to) Python compatible or implemental libraries, including the "cv2," "Imutils," "Time," "Collections," "Argparse," "Numpy," "sys," and "Scipy.spatial" libraries.

Various output metrics (e.g., as output by theseometer device 202) include, but are not limited to, total excursion, duration within radially concentric zones of 5 millimeters, time in central zone, latency to leave central zone, most peripheral zone reached, distance to origin, final position vector, X and Y variance (e.g., variance as illustrated in FIGS. 5 to 8 herein), dominant tremor frequency, and time spent in each quadrant (e.g., quadrants comprising −5.0 to 0.0 and 0.0 to 5.0 of X-position axis and Y-position axis, respectively, as illustrated in FIGS. 5 to 8 herein). The device (e.g., theseometer device 202) can also measure an individual's sensitivity to load through, e.g., a sinusoidal application of force while a subject is requested to maintain the pointing body appendage in a steady position.

Currently, neurological exams involve a casual assessment of pointing and holding or maintaining a particular body position. The interpretation of a subject's performance on conventional tests, however, is completely subjective, rendering comparative tests relatively useless and preventing the development of any standards for assessing performance. In contrast, the disclosed device (e.g., theseometer device 202) objectively quantifies proprioceptive performance, providing performance measures that can be subjected to comparative tests that will lead to standards of assessment. Use of the disclosed device, or theseometer (or proprioceptometer) (e.g., theseometer device 202), removes all subjectivity from the evaluation of an individual's ability to use and respond appropriately to proprioceptive input. It should be noted that proprioception is biased toward serving the motor system rather than sensory perception. Thus, healthy subjects will not perform perfectly and, for this reason, a control group of apparently healthy individuals is used to obtain baseline performance measures. This is illustrated, for example, for the disclosures and illustrations of each of FIGS. 3 through 8 herein.

In various embodiments, the invention (e.g., theseometer device 202) as disclosed herein measures an individual's ability to maintain a body position using proprioceptive input alone. It can also measure the sensitivity of a subject to load by comparing results both with and without a load in place. With the device (e.g., theseometer device 202), proprioceptive examinations can be tailored to lower limbs as well as fingers, wrists, elbows, and the chest. In some embodiments, the device (e.g., theseometer device 202) may also track lips for predicting, for example, early tardive dyskinesia. Thus, the output variables of the device (e.g., theseometer device 202) are clinically relevant and ethologically based. As one example of the device's ethological basis, the device may use polar coordinates rather than the Cartesian coordinates used by other proprioceptive-measuring equipment.

The invention (e.g., theseometer device 202) as disclosed herein is inexpensive, straightforward to manufacture, easy to use, and easily adapted to novel tasks. It can also be modified to test the lower limb. All of these advantages are attributable to the device's straightforward design. This gives the invention an inherent advantage over other devices, which are large, delicate, cumbersome, difficult to transport, and not easily grasped by non-experts. The invention integrates analysis into the device itself (e.g., via base unit 210 and its various components). Exceptional portability, due to its light weight and optional attached wheeling base (e.g., vehicle support 220), as well as its ability to be disassembled, is also unheard of in this niche of medical devices.

Another embodiment of the device comprises multiple targets of controllable availability, such as lighted (e.g., LED) targets that light up in a sequential fashion, with control provided by an electronic control board (e.g., an electronic control board of base unit 210). This embodiment is well-suited for tracking dynamic movement. One of the most common motor symptoms of subjects with a proprioceptive deficiency or abnormality is slowness of movement. Tracking an individual's movements from one position to another provides velocity information that is used in diagnostic and treatment assessment.

In various embodiments, the invention (e.g., theseometer device 202) quantifies proprioceptive performance. For example, software algorithms or scripts (e.g., software 216) and related libraries (e.g., software libraries 218), as described herein with respect to FIGS. 3 to 8, may quantify functional, ethologically valid characteristics of sensory motor performance. This may be performed as part of a casual assessment of an individual's pointing and holding abilities as part of a neurological exam.

Use of the invention (e.g., theseometer device 202) removes subjectivity, as compared with conventional tests, from the evaluation of an individual's ability to use and respond appropriately to proprioceptive input. It should be noted that even healthy subjects are not robotically perfect at the task. Using the device (e.g., theseometer device 202) to obtain objective measures of proprioceptive performance, a large number of control subjects of mixed sex, age, and demographics is assessed to determine the normal range for a given sex and/or age range.

In various embodiments, real time tracking may be performed using the Open Source Computer Vision Library ("OpenCV" called "cv2" here), which includes Python algorithms adapted to track the object of interest utilizing several parameters, as described below. A flowchart outlining the software logic used to implement the algorithms is illustrated in FIG. 3 and, for the assessment of tremor, FIG. 4.

Generally, in various embodiments, theseometer device 202 obtains video and/or images at a 30 frame-per-second frame rate utilizing the camera (e.g., digital camera 208) connected to the device. A Gaussian blur image adaptation may be applied by processor 212 to each individual frame. Color features may be extracted from the video and/or images through a HSV range threshold. Shape(s) may be detected, e.g., by processor 212, utilizing a histogram of oriented gradients (HOG). In some embodiments, a machine learning algorithm may be trained, by processor 212, with HOG descriptors. The HOG descriptors may be obtained from an XML file produced utilizing dlib's open source imglab graphical tool, from images and/or video of the object of interest (e.g., an individual or body part against distinguishable target mark 206) obtained in different backgrounds, in order to produce a custom object detector or mapping to detect or track movement or positions of the object of interest.

Iterations of erosion and dilation of detected pixels of images and/or video, as capture or recorded by, e.g., digital camera 208, may be performed in order to reduce noise. Feature extraction may be performed, e.g., by processor 212, to determine or compute shape, and precise and/or accurate X, Y position(s) of a subject (e.g., a body part) may be obtained by computing the centroid of the detected object. This approach allows for positional precision down to the scale of individual pixels within the captured video and/or images. In some embodiments, a Continuously Adaptive Mean Shift (Camshift) algorithm may be implemented, e.g., by processor 212 executing software 216, to detect any Z component of the movement by updating a size of the window based on the perimeter of the detected object. The Z component allows for 3D movement analysis.

A variety of analyses are suitable for translating the data, with one approach to the analysis of output accomplished using an R script that reads the X and Y coordinate and calculates, for all conditions: a) The starting point of the tracking, with the starting point being defined as the center of the tracking (coordinates 0, 0); b) The difference in X, Y position between each frame and the previous frame. The software then calculates the magnitude and the direction of the change between sequential frames; c) total excursion (sum of vector magnitudes), mean distance across frames, variance in the X and Y direction; d) Sum of the direction component of the vectors to calculate the final vector angle and the mean angle of the movement; e) Percent of time spent in each quadrant, in relation to the center of the tracking. In addition, the script calculates percentage of time spent in zones that are defined as concentric circumferences (also centered at the center of the tracking) with radii that increased in 5 mm increments, e.g., as associated with distinguishable target mark 206. Output also includes the outermost zone reached and latency to leave the central zone.

Comparative graphs of X, Y position across frames of images and/or video, and a Fast Fourier Transformation (FFT) histogram to obtain descriptors of dominant frequencies of possible tremors my also generated by processor 212 and/or base unit 210, each of the comparative graphs resembling, or being similar, to those described or illustrated herein for any of FIGS. 5 through 8.

In various embodiments, for example, including those implementing RASPBERRY PI hardware and/or components as described herein, software scripts and/or libraries (e.g., software 216 and/or software libraries 218) may be implemented to determine or otherwise measure proprioceptive performance or tremors in humans, as described herein. In such embodiments, the software scripts may implement a NerveMetric based test. For example, the software scripts and/or libraries may be executed or implemented by processor 212 or otherwise base unit 210 to implement the algorithms, methods, or scripts of FIGS. 3 and 4 described herein.

In such embodiments, a software script, may be implemented, for example, in the Python programming language (e.g., as software 216) and may be compiled with, interpreted with, or otherwise composed of software libraries (e.g., software libraries 218) for performing image and movement analysis, but not limited to "cv2," "Imutils,"

"Time," "Collections," "Argparse," "Numpy," "sys," and "Scipy.spatial" software libraries. In various embodiments, a theseometer device (e.g., theseometer device 202) may use and/or implement these libraries (e.g., software libraries 218) to perform the functionality as described herein, including, for FIGS. 3 and 4. For example, the "Argparse" module program can be run in different states, for example on a video or can initiate the digital camera 208.

A "Deque" class may be imported and incorporated into software scripts (e.g. software 216) for execution, for example, of the algorithms of FIGS. 3 and 4. Deque is a Python class or function executable or implementable by processor 212 to provide structure for tracking a trail, e.g., on a screen. In particular, the Deque class can be used by theseometer device 202 and/or processor 212 to draw or track a "contrail" which can trace a body part moving or otherwise positioned within in 2 dimensional (2D) or three dimensional (3D) space.

In various embodiments, theseometer device 202 and/or processor 212 may execute or implement the "Imutils" library to process images or videos (e.g., video frames or images) as described herein, including to resize frames or images, to processor image contours, and/or provide access to, or allow capture of, video or images, including video streams and video capture, e.g., via a webcam or digital camera 208, etc.

In various embodiments, theseometer device 202 and/or processor 212 may execute or implement the "Time" library to prepare or configure timing of the video or webcam (e.g., digital camera 208) for or before the recording, gathering, or capturing of frames begins.

In various embodiments, theseometer device 202 and/or processor 212 may execute or implement the "Argparse," which is a general purpose library, to manage command line arguments. For example, a software script may use Argparse to accept user input to configure the theseometer device 202 for capturing images or video for analysis and/or processing as described herein.

In various embodiments, theseometer device 202 and/or processor 212 may execute or implement the "cv2" library (which is also be referred to herein as the "cv2" library and is also called "OpenCV") to manage, process, and/or analyze image and video frames, which may include to digitally recognize or determine color(s) of pixel(s) within images and video frames, and implement morphology, masking, blurring, contour creation, and other such image manipulation or generation for processing and/or displaying image(s) or video frames.

In various embodiments, theseometer device 202 and/or processor 212 may execute or implement a "CentroidTracker" library, or module, to track of individual objects (e.g., body parts) by way of Euclidean distances. For example, theseometer device 202 may track an object's bounding box with inputs (e.g., images, contours, and/or image pixels) provided to the "CentroidTracker" library. Theseometer device 202 and/or processor 212 may also execute or implement the "CentroidTracker" library to compute or determine the centroid of the object. For each consecutive frame, the coordinates and/or centroid of the object may be updated using the Euclidean distance algorithm. Theseometer device 202 and/or processor 212 may also execute or implement the "CentroidTracker" library to handle objects that disappear and reappear within a set number of frames, such as 50 frames.

In various embodiments, theseometer device 202 and/or processor 212 may execute or implement the "Numpy" library to create or manage vectors of object centroids (e.g., centers of images associated with body parts determined or detected in the images) during tracking and to manipulate or generate result matrices during analysis.

In various embodiments, theseometer device 202 and/or processor 212 may execute or implement the Scipy.spatial library to compute or determine the Euclidean distance of a centroid (e.g., as determined with the Numpy library) from one frame to the next. Euclidean distance defines the ordinary straight-line distance between two points in Euclidean space, e.g., between two pixels, two contours, or other portions of an image in 2D or 3D space.

In embodiments implementing NerveMetric related software or code, the software script may be built on top of, use, incorporate, or otherwise comprise, a digital template for extracting a colored object (e.g., an image of an individual, body part of an individual, or other object described herein) from an image or video as generated by a video, webcam, or otherwise digital camera (e.g., digital camera 208). In addition, NerveMetric based code may also be implemented by processor 212 to label one or more contours in an image or video frame to differentiate among such frames. For example, the cv2 library may label and/or detect contours in an image, where contours may be defined as line(s) joining points along a boundary of an image that have a same or similar intensity. Generally, contours may be used (e.g., by processor 212) to determine shape analysis, find the size of the object of interest, and perform object detection in a frame or image. For example, cv2 has a "findContourO" function that may be implemented or called to extract one or more contours from image(s), and that may be used by theseometer device 202 to extract or detect contours of an individual, or contours of a body part of an image, for processing, analysis, or otherwise as described herein.

In addition, NerveMetric based code may also be extended to include GUI (graphic user interface) libraries where data from use of the theseometer device 202 can be displayed and saved using a touch screen. Arguments may be set with the GUI, including but not limited to captured images or movies, the captured range of concentric circles and the center of concentric circles. These arguments allow for on-the-spot, or real-time or live, software configuration regardless of the embodiment version chosen.

In addition, NerveMetric based code may also be implemented by processor 212 to track or follow a contour (or pixel or group of pixels) closest to a center (e.g., a center of distinguishable target mark 206), which would typically be the position of where an individual's body part (e.g., person's finger) is pointing, which may be tagged with a color per the digital template, distinguishable target mark 206, and/or contour analysis.

In additional embodiments, NerveMetric implementations, as implemented by base unit 210 and/or processor 212, may use machine learning, including implementation of neural networks, for object detection (e.g., body part detection). For example, a machine component, e.g., as generated and stored in memory 214, may be trained by processor 212 using a supervised or unsupervised machine learning program or algorithm. The machine learning program or algorithm may employ a neural network, which may be a convolutional neural network, a deep learning neural network, or a combined learning module or program that learns in two or more features or feature datasets in a particular areas of interest. The machine learning programs or algorithms may also include natural language processing, semantic analysis, automatic reasoning, regression analysis, support vector machine (SVM) analysis, decision tree analysis, random forest analysis, K-Nearest neighbor analysis, naïve Bayes analysis, clustering, reinforcement learning, and/or other machine learning algorithms and/or techniques. Machine learning may involve identifying and recognizing patterns in existing data (such as body parts of individuals in image or video frame data) in order to facilitate making predictions for subsequent data (to predict or determine movements or trajectories of individuals or body parts of individuals).

Machine learning model(s), such as those of trained herein, may be created and trained based upon example (e.g., "training data,") inputs or data (which may be termed "features" and "labels") in order to make valid and reliable predictions for new inputs, such as testing level or production level data or inputs. In supervised machine learning, a machine learning program operating on a server, computing device, or otherwise processor(s), may be provided with example inputs (e.g., "features") and their associated, or observed, outputs (e.g., "labels") in order for the machine learning program or algorithm to determine or discover rules, relationships, or otherwise machine learning "models" that map such inputs (e.g., "features") to the outputs (e.g., labels), for example, by determining and/or assigning weights or other metrics to the model across its various feature categories. Such rules, relationships, or otherwise models may then be provided subsequent inputs in order for the model, executing on the base unit 210, computing device, or otherwise processor(s), to predict, based on the discovered rules, relationships, or model, an expected output.

In unsupervised machine learning, the server, computing device, or otherwise processor(s), may be required to find its own structure in unlabeled example inputs, where, for example multiple training iterations are executed by the base unit, computing device, or otherwise processor(s) to train multiple generations of models until a satisfactory model, e.g., a model that provides sufficient prediction accuracy when given test level or production level data or inputs, is generated. The disclosures herein may use one or both of such supervised or unsupervised machine learning techniques.

In such machine learning based embodiments, for example, contours and/or pixels as detected, extracted, or otherwise determined from one or more image or frames of an individual or body party of individual positioned together with distinguishable target mark 206 may be used as feature data to train a machine learning model to detect position(s) of the individual or body party over time for purposes of measuring proprioceptive performance or tremor in humans, as described herein, for example, for FIGS. 3 and/or 4. For example, a machine component, e.g., as stored in memory 214, may be trained by processor 212 using a supervised or unsupervised machine learning program or algorithm.

As a further example, in some embodiments, a machine learning model may be trained (e.g., by processor 212) with a plurality of images depicting sets of distinguishable target marks (e.g., distinguishable target mark 206) and corresponding body parts of individuals positioned therewith. In such embodiments, processor 212 may implement the machine learning model to assess, by processor 212, a proprioceptive performance of an individual based on an analyzing, by processor 212, a position of a pointing body part of the individual relative to the distinguishable target mark.

Such machine learning (e.g., neural network) embodiments increase the versatility of NerveMetric based assessments of neural health, where the theseometer device (e.g., theseometer device 202) may be more accepting of (and/or more robust compared to) various frame backgrounds, where the distinguishable target mark 206 may be positioned with various backgrounds and body types, and the frames of the body parts or individual are captured (e.g., by digital camera 208) against such backgrounds. This allows for more robust, more accurate, and/or easier deployment and use of theseometer device 202 when detecting movement, positions, or tracking of an individual. In such embodiments, color tracking may be unnecessary.

In additional embodiments, NerveMetric implementations, as implemented by base unit 210 and/or processor 212, may use or incorporate a Z-coordinate, which provides depth perception, in addition to the X and Y coordinates (e.g., as illustrated by FIGS. 5 to 8). The Z-coordinate provides additional accuracy to the output of the theseometer device 202 because the additional depth dimension can further be used to track or analyze an individual's (or individual's body part's) movement or position for purpose of determining or otherwise measuring proprioceptive performance in humans, as described herein.

In some embodiments, the disclosed device (e.g., theseometer device 202) may track objects such as body parts (e.g., a fingertip) without the need for a tracking aid. Some embodiments provide algorithm processing speeds compatible with live tracking of body part movements using higher frame rates. The Nyquist sampling theorem reveals that in order to detect tremors with a frequency of 10-15 Hz, the sampling rate needs to be at least 20-30 Hz. Theseometer device 202, executing software 216, may accommodate frame rates of up to 60 Hz. Embodiments further comprising an informative printout or screen display containing results and the range of normal values for immediate assessment of proprioceptive and motor function is also contemplated. Examples of results from healthy individuals (FIG. 5 and FIG. 6) and ataxic patients (FIG. 7 and FIG. 8) with eyes open and closed, respectively, are provided herein.

In additional embodiments, a mobile device can also be used to mimic a proprioceptometer that measures tremor or proprioceptive performance as described herein. The user points at a target that is central to a series of concentric circles displayed on the screen of the mobile device while a tone of, e.g., 60 seconds, or the desired testing time, plays. The series of concentric circles may be displayed the screen in the same or similar manner as shown herein for distinguishable target mark 206. The user may be asked (e.g., via a display message on the screen or audible command from the mobile device) to point with eyes open and then again with eyes closed. The mobile device's camera may then be used to capture the movement of a body part, e.g., a finger movement, and an assessment of tremor or proprioceptive performance is provided to the user using the software logic in FIG. 4. The output may be provided to the person, or a physician, with an assessment of whether a tremor is present and, if so, what type of tremor is present. Additionally, or alternatively, the output may be provided to the person, or a physician, with an assessment of proprioceptive performance, including a degree, ranking, or other measure of proprioceptive performance.

In sum, the invention allows for the assessment of proprioceptive function. This can be used to diagnose motor and sensory disorders, such as the motor and/or sensory disorders of diabetic neuropathy, neurological trauma, or movement disorders (e.g., ataxia and Parkinson's disease), as well as to track recovery from trauma or surgical interventions.

Aspects of the Disclosure

1. A theseometer comprising (a) a clear planar material comprising a distinguishable target mark and at least three concentric rings disposed about the target mark; (b) a digital camera comprising a lens concentric to the distinguishable target mark; and (c) a base unit comprising an electronic processor and memory.

2. The theseometer of aspect 1 wherein the clear planar material is plastic.

3. The theseometer of aspect 2 wherein the plastic is poly (methyl methacrylate), butyrate, polycarbonate, polystyrene, or polyester.

4. The theseometer of aspect 1 wherein the clear planar material is rigid.

5. The theseometer of aspect 1 wherein the digital camera is attached to a support arm.

6. The theseometer of aspect 5 wherein the support arm is articulable.

7. The theseometer of aspect 1 wherein the base unit further comprises software for tracking the movement of a pointing body part.

8. The theseometer of aspect 1 wherein the base unit further comprises software for detecting a tremor in a pointing body part.

9. The theseometer of aspect 1 capable of measuring the distance between the end point of a pointing body part and the target mark to a precision within 1.0 millimeter.

10. A method of assessing the proprioceptive performance of an individual comprising: (a) having the individual use a pointing body part to point to a distinguishable target mark on the clear material of the device of aspect 1; (b) recording the position of the pointing body part; (c) analyzing the position of the pointing body part relative to the distinguishable target mark; and (d) assessing the proprioceptive performance of the individual based on the analysis.

11. The method of aspect 10 wherein the pointing body part is a fingertip, a finger, a hand, an arm, a shoulder, a toe, a foot, a leg, a head or a chin.

12. The method of aspect 10 wherein the position of the pointing body part is detected over time, resulting in the determination of a trajectory of the pointing body part.

13. The method of aspect 10 wherein the pointing body part is associated with an accessory pointing device.

14. The method of aspect 12 wherein the detection of the pointing body part over time results in the detection of a tremor.

15. The method of aspect 10 wherein the individual has diabetic neuropathy, neurological trauma, or a movement disorder.

16. The method of aspect 15 wherein the movement disorder is ataxia.

17. The method of aspect 15 wherein the movement disorder is Parkinson's disease.

18. The method of aspect 15 wherein the diabetic neuropathy, neurological trauma, or movement disorder was undiagnosed prior to assessing proprioceptive performance.

19. A theseometer device comprising: (a) a distinguishable target mark and a series of concentric rings disposed about the target mark, each of the distinguishable target mark and series of concentric rings exhibited via a planar surface; (b) a digital camera comprising a lens concentric to the distinguishable target mark; and (c) a base unit comprising an electronic processor and memory.

20. The theseometer device of aspect 19 wherein the planar surface is a clear planar material, and wherein the clear planar material is plastic.

21. The theseometer device of aspect 19 wherein the planar surface is a screen of a mobile device.

22. A method of assessing a proprioceptive performance of an individual comprising: (a) recording, into a memory of a theseometer device, a position of a pointing body part of the individual, the theseometer device comprising a distinguishable target mark and a series of concentric rings disposed about the target mark, each of the distinguishable target mark and series of concentric rings exhibited via a planar surface, and wherein the individual points with the pointing body part to the distinguishable target mark; (b) analyzing, by a processor, the position of the pointing body part relative to the distinguishable target mark; and (c) assessing, by the processor, the proprioceptive performance of the individual based on the analysis of the pointing body part relative to the distinguishable target mark.

23. The method of aspect 22 further comprising training a machine learning model with a plurality of images depicting sets of distinguishable target marks and corresponding body parts of individuals, wherein the processor implements the machine learning model to assess, by the processor, the proprioceptive performance of the individual based on the analysis.

The foregoing aspects of the disclosure are exemplary only and not intended to limit the scope of the disclosure.

Additional Considerations

Each of the references cited herein is hereby incorporated by reference in its entirety or in relevant part, as would be apparent from the context of the citation.

It is to be understood that while the claimed subject matter has been described in conjunction with the detailed description thereof, the foregoing description is intended to illustrate and not limit the scope of that claimed subject matter, which is defined by the scope of the appended claims. Other aspects, advantages, and modifications are within the scope of the following claims.

Although the disclosure herein sets forth a detailed description of numerous different embodiments, it should be understood that the legal scope of the description is defined by the words of the claims set forth at the end of this and equivalents. The detailed description is to be construed as exemplary only and does not describe every possible embodiment since describing every possible embodiment would be impractical. Numerous alternative embodiments may be implemented, using either current technology or technology developed after the filing date of this patent, which would still fall within the scope of the claims.

The following additional considerations apply to the foregoing discussion. Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

Additionally, certain embodiments are described herein as including logic or a number of routines, subroutines, applications, or instructions. These may constitute either software (e.g., code embodied on a machine-readable medium or in a transmission signal) or hardware. In hardware, the routines, etc., are tangible units capable of performing certain operations and may be configured or arranged in a certain manner. In example embodiments, one or more computer systems (e.g., a standalone, client or server computer system) or one or more hardware modules of a computer system (e.g., a processor or a group of processors) may be configured by software (e.g., an application or application portion) as a hardware module that operates to perform certain operations as described herein.

In various embodiments, a hardware module may be implemented mechanically or electronically. For example, a hardware module may comprise dedicated circuitry or logic that is permanently configured (e.g., as a special-purpose processor, such as a field programmable gate array (FPGA) or an application-specific integrated circuit (ASIC)) to perform certain operations. A hardware module may also comprise programmable logic or circuitry (e.g., as encompassed within a general-purpose processor or other programmable processor) that is temporarily configured by software to perform certain operations. It will be appreciated that the decision to implement a hardware module mechanically, in dedicated and permanently configured circuitry, or in temporarily configured circuitry (e.g., configured by software) may be driven by cost and time considerations.

Accordingly, the term "hardware module" should be understood to encompass a tangible entity, be that an entity that is physically constructed, permanently configured (e.g., hardwired), or temporarily configured (e.g., programmed) to operate in a certain manner or to perform certain operations described herein. Considering embodiments in which hardware modules are temporarily configured (e.g., programmed), each of the hardware modules need not be configured or instantiated at any one instance in time. For example, where the hardware modules comprise a general-purpose processor configured using software, the general-purpose processor may be configured as respective different hardware modules at different times. Software may accordingly configure a processor, for example, to constitute a particular hardware module at one instance of time and to constitute a different hardware module at a different instance of time.

Hardware modules may provide information to, and receive information from, other hardware modules. Accordingly, the described hardware modules may be regarded as being communicatively coupled. Where multiple of such hardware modules exist contemporaneously, communications may be achieved through signal transmission (e.g., over appropriate circuits and buses) that connect the hardware modules. In embodiments in which multiple hardware modules are configured or instantiated at different times, communications between such hardware modules may be achieved, for example, through the storage and retrieval of information in memory structures to which the multiple hardware modules have access. For example, one hardware module may perform an operation and store the output of that operation in a memory device to which it is communicatively coupled. A further hardware module may then, at a later time, access the memory device to retrieve and process the stored output. Hardware modules may also initiate communications with input or output devices, and may operate on a resource (e.g., a collection of information).

The various operations of example methods described herein may be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions. The modules referred to herein may, in some example embodiments, comprise processor-implemented modules.

Similarly, the methods or routines described herein may be at least partially processor-implemented. For example, at least some of the operations of a method may be performed by one or more processors or processor-implemented hardware modules. The performance of certain of the operations may be distributed among the one or more processors, not only residing within a single machine, but deployed across a number of machines. In some example embodiments, the processor or processors may be located in a single location, while in other embodiments the processors may be distributed across a number of locations.

The performance of certain of the operations may be distributed among the one or more processors, not only residing within a single machine, but deployed across a number of machines. In some example embodiments, the one or more processors or processor-implemented modules may be located in a single geographic location (e.g., within a home environment, an office environment, or a server farm). In other embodiments, the one or more processors or processor-implemented modules may be distributed across a number of geographic locations.

This detailed description is to be construed as exemplary only and does not describe every possible embodiment, as describing every possible embodiment would be impractical, if not impossible. A person of ordinary skill in the art may implement numerous alternate embodiments, using either current technology or technology developed after the filing date of this application.

Those of ordinary skill in the art will recognize that a wide variety of modifications, alterations, and combinations can be made with respect to the above described embodiments without departing from the scope of the invention, and that such modifications, alterations, and combinations are to be viewed as being within the ambit of the inventive concept.

The patent claims at the end of this patent application are not intended to be construed under 35 U.S.C. § 112(f) unless traditional means-plus-function language is expressly recited, such as "means for" or "step for" language being explicitly recited in the claim(s). The systems and methods described herein are directed to an improvement to computer functionality, and improve the functioning of conventional computers.

What is claimed is:

1. A theseometer device comprising:
   (a) a distinguishable target mark and a series of concentric rings disposed about the distinguishable target mark, each of the distinguishable target mark and series of concentric rings exhibited via a planar surface;
   (b) a digital camera comprising a lens concentric to the distinguishable target mark;
   (c) a base unit comprising an electronic processor and memory; and
   (d) instructions stored on the memory and configured for execution by the electronic processor that, when executed by the electronic processor, cause the electronic processor to:
   determine a proprioceptive performance of an individual based on analysis of a pointing body part of the individual relative to the distinguishable target mark.

2. The theseometer device of claim 1 wherein the planar surface is a clear planar material, and wherein the clear planar material is plastic.

3. The theseometer device of claim 2 wherein the plastic is at least one of poly (methyl methacrylate), butyrate, polycarbonate, polystyrene, or polyester.

4. The theseometer device of claim 2 wherein the clear planar material is rigid.

5. The theseometer device of claim 1 wherein the planar surface is a screen of a mobile device.

6. The theseometer device of claim 1 wherein the digital camera is attached to a support arm.

7. The theseometer device of claim 6 wherein the support arm is articulable.

8. The theseometer of claim 1 wherein the base unit further comprises software for tracking movement of a pointing body part.

9. The theseometer device of claim 1 wherein the base unit further comprises software for detecting a tremor in a pointing body part.

10. The theseometer device of claim 1 is configured to measure a distance between an end point of a pointing body part and the target mark to a precision within 1.0 millimeter.

11. A method of using a theseometer device comprising:
capturing, by a digital camera associated with the theseometer device, one or more images of an individual, wherein the digital camera comprises a lens concentric to a distinguishable target mark, and wherein the distinguishable target mark is exhibited via a planar surface and comprises a series of concentric rings disposed about the distinguishable target mark; and
determining, by instructions stored on a memory and configured for execution by an electronic processor associated with the theseometer device, a proprioceptive performance of the individual based on analysis of a pointing body part of the individual relative to the distinguishable target mark.

12. The method of claim 11 wherein the planar surface is a clear planar material, and wherein the clear planar material is plastic.

13. The method of claim 12 wherein the plastic is at least one of poly (methyl methacrylate), butyrate, polycarbonate, polystyrene, or polyester.

14. The method of claim 12 wherein the clear planar material is rigid.

15. The method of claim 11 wherein the planar surface is a screen of a mobile device.

16. The method of claim 11 wherein the digital camera is attached to a support arm.

17. The method of claim 16 wherein the support arm is articulable.

18. The method of claim 11 wherein the base unit further comprises software for tracking movement of a pointing body part.

19. The method of claim 11 wherein the memory further comprises software for detecting a tremor in a pointing body part.

20. The method of claim 11 is configured to measure a distance between an end point of a pointing body part and the target mark to a precision within 1.0 millimeter.

* * * * *